United States Patent [19]
Weisman

[11] Patent Number: 5,888,514
[45] Date of Patent: Mar. 30, 1999

[54] NATURAL COMPOSITION FOR TREATING BONE OR JOINT INFLAMMATION

[76] Inventor: Bernard Weisman, 17061 Windsor Park Ct., Boca Raton, Fla. 33496-1634

[21] Appl. No.: 862,513

[22] Filed: May 23, 1997

[51] Int. Cl.$^6$ .......................... A61K 31/70; A61K 31/715; A61K 35/78; A61K 35/56

[52] U.S. Cl. ...................... 424/195.1; 424/196.1; 424/523; 424/547; 424/556; 514/54; 514/62; 514/474

[58] Field of Search ................... 424/195.1, 196.1, 424/523, 547, 556; 514/54, 62, 474

*Primary Examiner*—Theodore J. Criares
*Attorney, Agent, or Firm*—Hoffman & Baron, LLP; Irving N. Feit

[57] ABSTRACT

A composition for treating a mammal having a condition characterized by bone or joint inflammation comprises:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acid
1,000 mg chondroitin polysulfate,
100 mg extract of sea cucumber,
300 mg black currant seed oil,
3,500 mg ascorbic acid (vitamin C),
150 mg pyridoxine HCl (vitamin B6),
1,000 mg devil's claw powder.

1 Claim, No Drawings

NATURAL COMPOSITION FOR TREATING BONE OR JOINT INFLAMMATION

BACKGROUND

This invention relates to a mixture of natural ingredients for the treatment of bone or joint inflammation.

Bone and joint inflammation is a scourge of both animals and humans. Examples of this debilitating condition include arthritis, including rheumatoid arthritis, rheumatism, tendonitis, etc.

Those who suffer from bone or joint inflammation experience pain and discomfort, and may, in advanced cases, lose the effective use of inflamed joints. The goal of therapeutic methods for treating bone or joint inflammation is the relief of pain and discomfort, and the restoration of use of inflamed joints.

Most western countries have adopted traditional western medicine to treat bone and joint inflammation. The treatments usually involve synthetic drugs, such as Motrin, Fildene, Indocin, Clinoril, Naprosyn, Vicoden, and Meclomen. These drugs do not always alleviate pain and discomfort, or restore significant use of inflamed joints. Moreover, such drugs may lead to undesirable side effects.

Natural ingredients, including Ayurvedic formulations, have also been used to treat bone and joint inflammation, especially in eastern countries, and, increasingly, in western countries. Such natural ingredients include cartilage, glucosamine sulfate, proteolytic and other enzymes, and herbs, such as the gummy extract of Boswellia serrata, Ashwagandha, and ginseng. While not leading to the kinds of side effects observed with western drugs, the eastern formulations do not always provide sufficient relief of pain and discomfort, or restore significant use of inflamed joints.

There is, therefore, a need for new treatments of conditions characterized by inflamed bone or joints that avoid the disadvantages of known treatments, including the disadvantages described above. It is an objective of the present invention to provide such new treatments. More specifically, it is an objective of the present invention to provide new treatments for bone or joint inflammation that are able to relieve pain and discomfort, and to restore significant use of inflammed joints, better than known methods, while at the same time avoiding the side effects observed with traditional drugs.

SUMMARY OF THE INVENTION

These and other objectives, as will be apparent to those having ordinary skill in the art, have been met by providing a novel composition for treating mammals having conditions characterized by bone or joint inflammation. The composition is formed by preparing a mixture comprising an effective amount of systemically absorbable cartilage, and an effective amount of an aminosaccharide. The composition optionally further comprises one, or any combination of, an effective amount of a mucopolysaccharide; proteolytic enzymes; one or more extracts of an herb of the genus Withenia, of the bark of an herb of the genus Salix, or of a root of an herb of the genus Panax; boswellic acid or its derivatives; chondroitin; an extract of sea cucumber; black currant oil; ascorbic acid (vitamin C); pyridoxine hydrochloride (vitamine B6); a secondary root of a plant from the genus Harpagophytum; L proline; or papain.

DETAILED DESCRIPTION OF THE INVENTION

It has now surprisingly been discovered that compositions formed by preparing mixtures of known components are able to act efficiently in the treatment of conditions characterized by bone or joint inflammation. The mixture consists of mostly natural components, and preferably consists of all natural components. A "natural component" is component that is found in nature.

The components may be mixed in any order to prepare the composition. The composition may comprise the same components that were added to the mixture, or any components that result from an interaction between two or more of the components after mixing.

All conditions characterized by bone or joint inflammation are able to benefit from the composition of the invention. These conditions include, for example, all forms of arthritis, rheumatism, including rheumatoid arthritis, bursitis, tendonitis, gout, etc. The composition is effective for all mammals, including farm animals, laboratory animals, pet animals, and humans.

The components of the composition are in a form that are systemically absorbable in a mammal. The components are preferably soluble. After being absorbed, the cartilage and other components of the composition, or their metabolic products, are delivered to the inflamed bone or joints.

The compositions are formulated for systemic administration to mammals. Any mode of systemic administration is suitable. Some examples include intravenous, intramuscular, and oral administration. The preferred mode of administration is oral administration.

The quantities of the various doses are described below in terms of unit doses. Mammals receive unit doses of the composition on the basis of various parameters, as is well known in the medical and veterinary arts. The parameters include, for example, size, sensitivity to the components, severity of the condition being treated, etc. One to three unit doses are normally administered one to four times a day.

The composition may be formulated, along with customary pharmaceutically acceptable excipients, in any form suitable for systemic administration. Some suitable forms include capsules, powders, liquids, and suspensions.

Each capsule contains a unit dose of each component. In the case of a powder, liquid, or suspension, a unit dose is considered, roughly, to be contained in a teaspoonful or a tablespoonful.

For the purpose of the present specification, an effective amount of a component is considered to be a unit dose in the case of a capsule. In the case of a powder, solution, or suspension, an effective amount is considered to be a multiple of the unit dose, calculated by multiplying the unit dose by the number of unit doses in a container. Of course, those having ordinary skill in the art could formulate comparable effective amounts based on a unit dose being contained in a volume other than that of a standard teaspoonful or a tablespoonful.

The components may be formulated for administration into one composition containing all the components. Alternatively, the components may be formulated into more than one composition, each of which contains one or more components. In addition, each component may constitute a separate composition, and be administered separately. It is preferable to administer the smallest number of separate compositions.

In the discussion below, all numbers are approximate, unless otherwise stated. The weights of extracts and concentrates do not include the weights of the solvents. Unless otherwise specified, extracts and concentrates are substantially saturated in the component or components being extracted.

The mixture contains systemically absorbable, preferably soluble, cartilage. The cartilage may be derived from any source, such as from mammals or fish. The preferred mammalian cartilage is bovine cartilage. A suitable source of soluble bovine cartilage is Enzymatic Therapy, Green Bay, Wis.

The preferred fish cartilage is selachian fish cartilage. The preferred selachian fish cartilage is shark cartilage, preferably soluble shark cartilage.

A particularly effective form of cartilage is a mixture of mammalian cartilage and fish cartilage. The mammalian cartilage is preferably bovine cartilage. The fish cartilage is preferably selachian fish cartilage, and more preferably shark cartilage. The fish cartilage preferably constitutes up to about 25%, more preferably up to about 20%, and most preferably about 10 to about 20% of the total cartilage.

The minimum unit dose of cartilage is about 1,500, preferably about 1800, and more preferably about 2000 mg. The maximum unit dose of cartilage is about 3,500, preferably about 3,000, and more preferably about 2,500 mg.

The cartilage is mixed with an aminosaccharide. Any aminosaccharide that is effective in combination with the cartilage is suitable. The aminosaccharide is preferably an aminomonosaccharide, more preferably a glucosamine, and more preferably glucosamine sulfate. A suitable source of aminosaccharide is GS-500 sold by Enzymatic Therapy, Green Bay, Wis.

The minimum unit dose of aminosaccharide is about 500, preferably about 700, and more preferably about 900 mg. The maximum unit dose of aminosaccharide is about 3,500, preferably about 3,000, and more preferably about 1,500 mg.

A preferred composition is formed by preparing a mixture comprising effective amounts of cartilage and aminosaccharide, as described above, and an effective amount of a mucopolysaccharide. The mucopolysaccharide is preferably a concentrate derived from connective tissue, preferably bovine connective tissue, more preferably tracheal connective tissue, and most preferably bovine tracheal connective tissue. A suitable source of mucopolysaccharide concentrate is Cardiovascular Research Ltd., Concord, Calif. The mucopolysaccharide may also be prepared by hydrolyzing beef tracheas with papain.

The minimum unit dose of mucopolysaccharide is about 100, preferably about 200, and more preferably about 300 mg. The maximum unit dose of mucopolysaccharide is about 1000, preferably about 500, and more preferably about 400 mg.

Another preferred composition is formed by preparing either of the mixtures described above, and an effective amount of one or more proteolytic enzymes. A suitable source of proteolytic enzymes is pancreatic extract (pancreatin), preferably hog pancreatic extract. It is desirable to use a full-strength, undiluted pancreatic extract (10X U.S.P.), preferably hog pancreatic extract. It is desirable for the units of activity of proteolytic enzymes to be about 50,000–200,000, preferably about 100,000.

It is also desirable for the extract to contain additional enzymes, such as amylase and lipase. It is desirable for the units of activities to be: amylase, 50,000–200,000, preferably about 100,000; and lipase 12,500–50,000, preferably about 25,000. Preferably, the ratio of units of activity of proteolytic enzymes, amylase, and lipase should be about 2–6:2–6:1.

It is also desirable to include other enzymes, such as papain, bromelain, trypsin, chymotrypsin, and lysozyme. A suitable source of proteolytic enzymes is sold in the form of tablets under the name Mega-Zyme from Enzymatic Therapy, Green Bay, Wis. Each tablet of Mega-Zyme contains the following enzymes: pancreatic enzymes (10X), 325 mg; trypsin, 75 mg; papain, 50 mg; bromelain, 50 mg; amylase, 10 mg; lipase, 10 mg; lysozyme, 10 mg; and chymotrypsin, 2 mg.

The minimum unit dose of proteolytic enzymes is about 100, preferably about 150, and more preferably about 200 mg. The maximum unit dose of proteolytic enzymes is about 400, preferably about 300, and more preferably about 250 mg.

Another preferred composition is formed by preparing any of the mixtures described above, and an effective amount of one or more extracts, preferably standardized extracts, of an herb of the genus Withenia, of the bark of an herb of the genus Salix, or of a root of an herb of the genus Panax. The herb of the genus Withenia is preferably derived from the species somnifera (ashwagandha). The bark of an herb of the genus Salix is preferably willow bark. The root of an herb of the genus Panax is preferably gensing. See, for example, Analbagan et al, Ind. J. Exp. Biol. 19, 245 (1981) and Jamieson et al, Can. J. Biochem. 53, 414 (1975).

The minimum unit dose of the extracts of an herb of the genus Withenia, of the bark of an herb of the genus Salix, or of a root of an herb of the genus Panax is about 150, preferably about 250, more preferably about 350 mg. The maximum unit dose of the extracts is about 2,000, preferably about 1,200, and more preferably about 800 mg. The bark of an herb of the genus Salix and the root of an herb of the genus Panax may also be cut into pieces or ground into a powder. Grinding into a powder is preferred.

Another preferred composition is formed by preparing any of the mixtures described above, and an effective amount of one or more isomers of boswellic acid or its derivatives. The isomers include alpha, beta, and 11-keto-beta boswellic acid. Derivatives include the acetyl derivatives.

The isomers of boswellic acid and its derivatives are preferably naturally occuring, and may be derived from sources known in the art. They may, for example, be synthesized, or obtained from aqueous or ethanolic extracts of an herb of the genus Boswellia, preferably from the gum resin of the species serrata. See, for example, Sen et al, Carbohydrate Res. 223, 321 (1992) and Ammon et al, Planta Med. 57, 203 (1991).

A suitable source of boswellic acids is an extract of Boswellia serrata resin standardized to 60% boswellic acids. Such an extract is available from Ayush Herbs, Inc., Bellevue, Wash. under the name Boswelya Plus. Each unit dose of Boswelya Plus contains boswellic acid (150 mg), ginger (100 mg), tumeric (50 mg), and winter cherry (ashwagandha) (100 mg).

The minimum unit dose of boswellic acids is about 50, preferably about 75, and more preferably about 100 mg. The maximum unit dose of boswellic acids is about 1,000, preferably about 500, and more preferably about 200 mg.

Another preferred composition is formed by preparing any of the mixtures described above, and an effective amount of chondroitin, preferably chondroitin polysulfate. The minimum unit dose of chondroitin is about 500, preferably about 700, and more preferably about 900 mg. The maximum unit dose of chondroitin is about 3,500, preferably about 3,000, and more preferably about 1,500 mg.

Another preferred composition is formed by preparing any of the mixtures described above, and an effective amount of an extract of sea cucumber preferably from the Australian coast. The minimum unit dose of sea cucumber is about 30, preferably about 60, and more preferably about 90 mg. The maximum unit dose of sea cucumber is about 400, preferably about 300, and more preferably about 150 mg.

Another preferred composition is formed by preparing any of the mixtures described above, and an effective amount of black currant oil, preferably black currant seed oil. The minimum unit dose of black currant oil is about 80, preferably about 150, and more preferably about 250 mg. The maximum unit dose of black currant oil is about 1,000, preferably about 500, and more preferably about 400 mg.

A suitable unit dose of black currant oil contains: GLA (about 45 mg), linoleic acid (about 95 mg), alpha-linolenic acid (about 34 mg), and stearidonic acid (about 9 mg).

A suitable source of black currant oil is Eclectic Institute, Inc. of Sandy, Oreg.

Another preferred composition is formed by preparing any of the mixtures described above, and an effective amount of ascorbic acid (vitamin C). The minimum unit dose of ascorbic acid is about 1,000, preferably about 2,000, and more preferably about 3,000 mg. The maximum unit dose of ascorbic acid is about 6,000, preferably about 5,000, and more preferably about 4,000 mg.

Another preferred composition is formed by preparing any of the mixtures described above, and an effective amount of pyridoxine HCl (vitamin B6). The minimum unit dose of pyridoxine HCl is about 30, preferably about 75, and more preferably about 125 mg. The maximum unit dose of pyridoxine HCl is about 700, preferably about 400, and more preferably about 200 mg.

Another preferred composition is formed by preparing any of the mixtures described above, and an effective amount of a secondary root (tuber) of a plant of the genus Harpagophytum. The plant is preferably from the species procumbens (devil's claw, also known as grapple plant). The secondary root may be extracted, cut into pieces, or ground into a powder. Grinding into a powder is preferred.

The minimum unit dose of the secondary root is about 70, preferably about 400, and more preferably about 800 mg of the secondary root. The maximum unit dose of the secondary root is about 3,500, preferably about 2,500, and more preferably about 1,500 mg of the secondary root.

Another preferred composition is formed by preparing any of the mixtures described above, and an effective amount of L-proline. The minimum unit dose of L-proline is about 80, preferably about 400, and more preferably about 600 mg. The maximum unit dose of L-proline is about 1,000, preferably about 900, and more preferably about 800 mg.

EXAMPLES

EXAMPLE 1

A composition is prepared by mixing unit doses of the following components:
2,250 mg soluble bovine cartilage,
250 mg soluble shark cartilage,
1,000 mg glucosamine sulfate.

EXAMPLE 2

A composition is prepared by mixing unit doses of the following components:
2,250 mg soluble bovine cartilage,
250 mg soluble shark cartilage,
1,000 mg glucosamine sulfate,
350 mg mucopolysaccharide concentrate.

EXAMPLE 3

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract.

EXAMPLE 4

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha.

EXAMPLE 5

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids.

EXAMPLE 6

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate.

EXAMPLE 7

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber.

EXAMPLE 8

A composition is prepared by mixing unit doses of the following components:
2,250 mg soluble bovine cartilage,
250 mg soluble shark cartilage,
1,000 mg glucosamine sulfate, 350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber,
300 mg black currant seed oil.

EXAMPLE 9

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber,
300 mg black currant seed oil,
3,500 mg ascorbic acid.

EXAMPLE 10

A composition is prepared by mixing unit doses of the following components:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber,
300 mg black currant seed oil,
3,500 mg ascorbic acid (vitamin C),
150 mg pyridoxine HCl (vitamin B6).

EXAMPLE 11

A composition is prepared by mixing unit doses of the following components:
2,250 mg soluble bovine cartilage,
250 mg soluble shark cartilage,
1,000 mg glucosamine sulfate,
350 mg mucopolysaccbaride concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber,
300 mg black currant seed oil,
3,500 mg ascorbic acid (vitamin C),
150 mg pyridoxine HCl (vitamin B6),
1,000 mg devil's claw powder.

EXAMPLE 12

A composition is prepared by mixing unit doses of the following components:
3,000 mg soluble shark cartilage, and
1,000 mg glucosamine sulfate.

EXAMPLE 13

A composition is prepared by mixing unit doses of the following components:
2,500 mg soluble bovine cartilage,
3,000 mg glucosamine sulfate, and
200 mg mucopolysaccharide concentrate.

EXAMPLE 14

A composition is prepared by mixing unit doses of the following components:
2,250 mg soluble bovine cartilage,
500 mg soluble shark cartilage,
2,000 mg glucosamine sulfate,
250 mg mucopolysaccharide concentrate,
500 mg proteolytic enzymes from hog pancreatic extract.

EXAMPLE 15

A composition is prepared by mixing unit doses of the following components:
4,000 mg soluble bovine cartilage,
300 mg soluble shark cartilage,
1,000 mg glucosamine sulfate,
700 mg mucopolysaccharide concentrate,
400 mg proteolytic enzymes from hog pancreatic extract,
1,000 mg standardized extract of ashwagandha.

EXAMPLE 16

A composition is prepared by mixing unit doses of the following components:
1,750 mg soluble bovine cartilage,
200 mg soluble shark cartilage,
3,000 mg glucosamine sulfate,
600 mg mucopolysaccharide concentrate,
500 mg proteolytic enzymes from hog pancreatic extract,
800 mg standardized extract of powdered willow bark.
670 mg extract of Boswellia serrata comprising 150 mg acetyl derivative of boswellic acids.

EXAMPLE 17

A composition is prepared by mixing unit doses of the following components:
1,850 mg soluble bovine cartilage,
600 mg soluble shark cartilage,
2,000 mg glucosamine sulfate,
500 mg mucopolysaccharide concentrate,
100 mg proteolytic enzymes from hog pancreatic extract,
700 mg standardized extract of gensing,
900 mg extract of Boswellia serrata comprising 150 mg boswellic acids,
5,000 mg chondroitin polysulfate.

EXAMPLE 18

A composition is prepared by mixing unit doses of the following components:
1,650 mg soluble bovine cartilage,
350 mg soluble shark cartilage,
4,000 mg glucosamine sulfate,
150 mg mucopolysaccharide concentrate,
400 mg proteolytic enzymes from hog pancreatic extract,
400 mg standardized extract of ashwagandha,
670 mg extract of Boswellia serrata comprising 150 mg Boswelya Plus
2,000 mg chondroitin polysulfate,
600 mg extract of sea cucumber.

EXAMPLE 19

A composition is prepared by mixing unit doses of the following components:
5,250 mg soluble bovine cartilage,
250 mg soluble shark cartilage,
500 mg glucosamine sulfate,
450 mg mucopolysaccharide concentrate,
300 mg MegaZyme,
750 mg standardized extract of ashwagandha,
350 mg extract of Boswellia serrata comprising 150 mg boswellic acids,
3,000 mg chondroitin polysulfate,
200 mg extract of sea cucumber,
100 mg black currant seed oil.

EXAMPLE 20

A composition is prepared by mixing unit doses of the following components:
1,900 mg soluble bovine cartilage,
500 mg soluble shark cartilage,
750 mg GS-500,
850 mg mucopolysaccharide concentrate,
150 mg proteolytic enzymes from hog pancreatic extract,
500 mg standardized extract of ashwagandha,
300 mg extract of Boswellia serrata comprising 150 mg boswellic acids,
3,000 mg chondroitin polysulfate,
200 mg extract of sea cucumber,
500 mg black currant seed oil,
1,500 mg ascorbic acid.

EXAMPLE 21

A composition is prepared by mixing unit doses of the following components:
8,000 mg soluble bovine cartilage,
500 mg soluble shark cartilage,
3,000 mg glucosamine sulfate,
700 mg mucopolysaccharide concentrate,
125 mg proteolytic enzymes from hog pancreatic extract,
400 mg standardized extract of ashwagandha,
370 mg extract of Boswellia serrata comprising 150 mg boswellic acids,
2,000 mg chondroitin polysulfate,
50 mg extract of sea cucumber,
600 mg black currant seed oil,
8,500 mg ascorbic acid (vitamin C),
450 mg pyridoxine HCl (vitamin B6).

EXAMPLE 22

A composition is prepared by mixing unit doses of the following components:
1,500 mg soluble hog cartilage,
500 mg soluble shark cartilage,
500 mg glucosamine sulfate,
500 mg mucopolysaccharide concentrate,
550 mg proteolytic enzymes from bovine pancreatic extract,
700 mg standardized extract of ashwagandha,
800 mg extract of Boswellia serrata comprising 150 mg boswellic acids,
3,000 mg chondroitin polysulfate,
100 mg extract of sea cucumber,
400 mg black currant seed oil,
6,500 mg ascorbic acid (vitamin C),
450 mg pyridoxine HCl (vitamin B6),
3,000 mg devil's claw powder.

I claim:

1. A composition for treating a mammal having a condition characterized by bone or joint inflammation, the composition being a mixture comprising:
2,250 mg soluble bovine cartilage,
250 mg soluble shark cartilage,
1,000 mg glucosamine sulfate,
350 mg mucopolysaccharide concentrate,
225 mg proteolytic enzymes from hog pancreatic extract,
500 mg standardized extract of ashwagandha,
470 mg extract of Boswellia serrata comprising 150 mg boswellic acids,
1,000 mg chondroitin polysulfate,
100 mg extract of sea cucumber,
300 mg black currant seed oil,
3,500 mg ascorbic acid,
150 mg pyridoxine HCl,
1,000 mg devil's claw powder.

* * * * *